(12) United States Patent
Lebon et al.

(10) Patent No.: US 9,782,367 B2
(45) Date of Patent: Oct. 10, 2017

(54) PROCESS FOR OBTAINING A MODAFINIL-BASED PHARMACEUTICAL COMPOSITION, RESULTING PHARMACEUTICAL COMPOSITION AND USE THEREOF

(71) Applicant: DEBREGEAS ET ASSOCIES PHARMA, Paris (FR)

(72) Inventors: Christophe Lebon, Rouvres (FR); Pascal Suplie, Montaure (FR); Fabrice Leboeuf, Saint-Max (FR); Jennifer Jung, Dieulouard (FR); Frantz Deschamps, Nancy (FR)

(73) Assignee: DEBREGEAS ET ASSOCIES PHARMA, Paris (FR)

( * ) Notice: Subject to any disclaimer, the term of this patent is extended or adjusted under 35 U.S.C. 154(b) by 0 days.

(21) Appl. No.: 14/381,699

(22) PCT Filed: Feb. 25, 2013

(86) PCT No.: PCT/FR2013/000051
§ 371 (c)(1),
(2) Date: Aug. 28, 2014

(87) PCT Pub. No.: WO2013/128087
PCT Pub. Date: Sep. 6, 2013

(65) Prior Publication Data
US 2015/0105470 A1 Apr. 16, 2015

(30) Foreign Application Priority Data
Feb. 28, 2012 (FR) ..................... 12 00580

(51) Int. Cl.
*A61K 9/14* (2006.01)
*A61K 31/165* (2006.01)
*A61K 9/16* (2006.01)
*A61K 9/20* (2006.01)

(52) U.S. Cl.
CPC .......... *A61K 31/165* (2013.01); *A61K 9/1623* (2013.01); *A61K 9/1676* (2013.01); *A61K 9/1682* (2013.01); *A61K 9/2018* (2013.01); *A61K 9/2077* (2013.01)

(58) Field of Classification Search
USPC ........................................... 424/489
See application file for complete search history.

(56) References Cited

U.S. PATENT DOCUMENTS

| 5,618,845 | A | 4/1997 | Grebow et al. | |
| 6,465,519 | B2 * | 10/2002 | Fu | 514/618 |
| 2006/0024370 | A1 | 2/2006 | Nguyen et al. | |
| 2007/0275057 | A1 | 11/2007 | Shawer et al. | |
| 2008/0317862 | A1 * | 12/2008 | Collingwood et al. | 424/489 |

FOREIGN PATENT DOCUMENTS

WO WO 2007/013962 A2 2/2007

OTHER PUBLICATIONS

Sonoda (Chem. Pharm. Bull. 57(10) 1040-1044 (2009).*
Wahl (Chapter 6 of Handbook of Pharmaceutical Granulation Technology, Third Edition (Drugs and the Pharmaceutical Sciences), CRC Press, Nov. 24, 2009, pp. 126-137).*
Arieda (The 2006 Annual AICHE Meeting. 2006, pp. 1-11).*
International Search Report issued in International Application No. PCT/FR2013/000051 dated May 8, 2013.
Written Opinion of the International Searching Authority issued in International Application No. PCT/FR2013/000051 dated May 8, 2013.
Sep. 2, 2014 International Preliminary Report on Patentability issued in International Application No. PCT/FR2013/000051 (with English Translation).

* cited by examiner

*Primary Examiner* — Devang Thakor
(74) *Attorney, Agent, or Firm* — Oliff PLC (57) ABSTRACT

The present invention relates to a novel method for obtaining a pharmaceutical composition based on modafinil. This method consists of solubilizing S modafinil in a fluid in the supercritical state and then after expansion of said fluid, recovering S modafinil by causing it to be absorbed at the surface by a support appearing as granules. Said fluid may be $CO_2$ or another solvent and the support, anhydrous lactose or mannitol. Application of the pharmaceutical composition in the cases when increased short term alertness and over a short period is required for the consumer of the pharmaceutical composition.

10 Claims, 12 Drawing Sheets

PROCESS FOR OBTAINING A MODAFINIL-BASED PHARMACEUTICAL COMPOSITION, RESULTING PHARMACEUTICAL COMPOSITION AND USE THEREOF

Modafinil is 2-[(diphenylmethyl)sulfinyl)]acetamide, the molecular formula is $C_{15}H_{15}NO_2S$ and its structural formula:

In 1970, benzhydryl sulfinyl derivatives were developed in France by the pharmaceutical laboratories Lafon. In 1986, Adrafinil was tested in the treatment of narcolepsy and abandoned because of problems of a gastro-intestinal nature, a rash phenomenon and significant skin allergies. Modafinil is a wakening drug used in Europe since 1992; it increases the wakening and diurnal alertness levels and is thus presently prescribed in the treatment of narcolepsy. The mode of action is not totally explained but involves an inhibition of the recapture of noradrenaline at sleep-inducing nuclei of the pre-optic ventrolateral nucleus; it would also have an adrenergic alpha 1 agonistic effect, a positive effect on glutamatergic transmission and it binds to the carrier of dopamine and reduces its recapture.

It is marketed under the names of Modiodal, Provigil and Alertec. The administered dose varies from a taking of 100 mg to two takings of 200 mg per day; the elimination half life is of about 14 hours in humans.

Modafinil is distributed in its racemic form which has a chiral center which in fact is a sulfur atom; however there exist two optically active isomers: the dextro-rotatory enantiomer and the levo-rotatory form, both of these forms being a priori present in equal amounts in the racemic form.

Both enantiomers have the same pharmacological activity in animals. However in humans, the levo-rotatory enantiomer (R) has a half-life from 10 to 14 hours; the dextro-rotatory enantiomer (S) as for it has a half-life from 3 to 4 hours [bibliographic reference: Wong et al., J.Clin. pharmacol., 39:30-40 (1999); Wong et al., J.Clin. pharmacol., 39:281-288(1999); Robertson et al., Clin. Pharmacokinet., 42:123-137 (2003)].

After administration, the R enantiomer would have a larger AUC than the racemic form and less variability in plasma levels.

Modafinil is used as a treatment of excessive diurnal somnolence associated with narcolepsy with or without catalepsy. Excessive diurnal somnolence is characterized by a difficulty in remaining awake and by an increase in falling asleep occurrences occurring at untimely moments. The recommended initial dose is 200 mg per day administered in a single taking in the morning or two takings in the morning and at noon according to the response of the patient. The doses may be increased up to 600 mg for patients having insufficient response.

The problem of the presently available commercial forms lies in the persistence of the effect of modafinil well beyond the period desired by the patients and even this remanence of alertness is finally of a nature perturbing the normal sleep cycle of the patient and may even induce insomnia.

Modafinil has also been successfully used in children in the treatment of ADHD (attention deficit hyperactivity disorder); in all these pathologies, strong variability is observed as regards clinical signs and it therefore proves to be necessary to proceed with individual therapeutic adjustment.

An object of the present invention is to make available to the patient a novel oral medicinal form of S modafinil having increased bioavailability as compared with the racemic form and a shortened duration of action.

One of the goals of the present invention is also to provide a formulation capable of meeting the strong interindividual variability and therefore to make available a homothetic formulation allowing easy adjustment of the administered dose.

Another object of the invention is to make available to the patient, a therapeutic preparation allowing a very fast therapeutic effect as compared with the racemic form and as compared with the S enantiomer administered alone.

Thus, the present invention relates to oral therapeutic forms of S Modafinil appearing as tablets, sachets or else in the form of gelatin capsules with doses between 25 and 200 mg of active ingredient, S modafinil, and preferentially from 50 to 100 mg.

The formulations presented here are homothetic and are therefore identical regardless of the dosages administered to the patient, which contributes to decreasing the strong variability reported earlier.

The compositions which will be described have been specifically developed so as to obtain in vitro very fast dissolution and in every case greater than that obtained with a form marketed on the market; a discriminating dissolution method was therefore specifically developed and allowed selection of the excipients and manufacturing processes.

Many oral formulations of modafinil are described in the prior art; thus patent U.S. Pat. No. 7,297,346 describes a modafinil composition, comprising lactose, maize starch, magnesium silicate, sodium croscarmellose, PVP, talcum and magnesium stearate.

This composition uses modafinil in its racemic form and corresponds to the commercial formulation Provigil.

The text US No. RE37516 presents pharmaceutical compositions using particles with a well-defined grain size, and particularly compositions for which 95% of the particles have a size of less than 200 microns. In this document, the obtained pharmacological effect is directly related to and dependent on the size of the final particles of the active ingredient; it is thus described that particles with a defined grain size are obtained by multiple successive milling and sifting operations. These operations are unwieldy and tedious and difficult to economically reconcile with the reality of industrial production. The method of the formulation, object of the present invention, uses quite another technique, a so-called supercritical fluid technique which will be described later on.

The family of patents U.S. Pat. No. 6,919,378, U.S. Pat. No. 6,489,363 and EP 1 562 572 B1 aims at administration in the form of preferentially non-aqueous solutions, the scope of which is very wide: solutions appearing as a mixture of two or several substances, said solutions may be in the form of a solid dispersed in a liquid, a solid or a semi-solid medium. Thus, patent EP 1 562 572 mentions a solid dispersion comprising at least one solid support, this same support belonging to the family of PEGs with a molecular weight comprised between 3,000 and 8,000 daltons, PEG 400 having been excluded.

Patent U.S. Pat. No. 6,919,378 describes non-aqueous compositions. Patent U.S. Pat. No. 6,489,363, as for it, describes a pharmaceutical composition comprising modafinil in solution, preferentially a non-aqueous solution, but aqueous compositions are also claimed.

Patent application US 2007/0275057 describes an oral composition comprising one or several pharmaceutical excipients in which at least 65% of the modafinil particles have a diameter of more than 220 microns. In the composition, object of the present invention, S modafinil is solubilized in a supercritical fluid and then crystallized on a support after expansion of the fluid. In this method, the particles of S modafinil obtained are of the order of one micron.

Patent EP 1 542 666 describes a pharmaceutical composition comprising at least two populations of modafinil particles with limited dimension ranges, some of these ranges being excluded from the final pharmaceutical composition. This assumes, in terms of manufacturing, several steps for separation and grain size inspections and involves a long and difficult process.

Patent application US 2004/0121003 describes a particular method for obtaining a mixture of an active ingredient and of at least one excipient with an average size comprising 10 and 500 microns; this same mixture being milled (air jet milling) for maintaining the size and the aspect of the individual particles.

International patent application WO 2008/008879 relates to compositions of nanoparticles comprising modafinil or one of its salts and at least one surface stabilizing agent absorbed on the same nanoparticles; the average grain size of the particles is of at least 2,000 nm. In the compositions of the present invention, the active ingredient is solubilized in the supercritical fluid and is then absorbed on a support.

The present invention will now be better understood by means of the facts which follow.

Modafinil appears as a crystalline white powder practically insoluble in water and partly soluble in methanol and acetone. The result of this is low bioavailability of modafinil; it is estimated to be about 40%; indeed the solubility of modafinil is too low, the absolute bioavailability was not able to be determined.

Thus, it was sought to improve the solubility of modafinil; in particular, and this is one of the objects of the invention, the solubility of modafinil was studied in supercritical fluids.

From among these supercritical fluids, mention may be made of $CO_2$: the technology of supercritical $CO_2$ is based on the solvent power of $CO_2$ which may be modulated at will depending on the pressure and temperature conditions applied to it.

In the supercritical state (more than 74 bars and 31° C.), $CO_2$ has very particular properties. The obtained fluid is characterized by great diffusivity (of the order of that of gases), which gives its good capability for diffusion, and a high density which provides it with a significant transport and extraction capacity.

A method for extraction with supercritical $CO_2$ operates in a closed circuit. It includes pressurizing units (pumps) and a temperature-setting unit (exchangers) in order to bring $CO_2$ above its critical point.

The product to be treated is placed in an extractor crossed by the supercritical $CO_2$ flow. Molecules which are soluble in supercritical $CO_2$, therefore extractable, are not very polar compounds with a low molecular mass.

The supercritical fluid has several advantages as compared with a liquid fluid:

a great diffusivity coefficient and a small viscosity coefficient;

an absence of surface tension, which increases the penetration power of the supercritical fluid.

A supercritical fluid has another advantage as compared with other solvents: its solubility changes depending on whether its temperature or its pressure is varied. Thus it is possible to ensure that it be a solvent for certain substances at a given moment and not at all, at the next instant. This facilitates recovery of the substance which has been dissolved.

Figure 1:
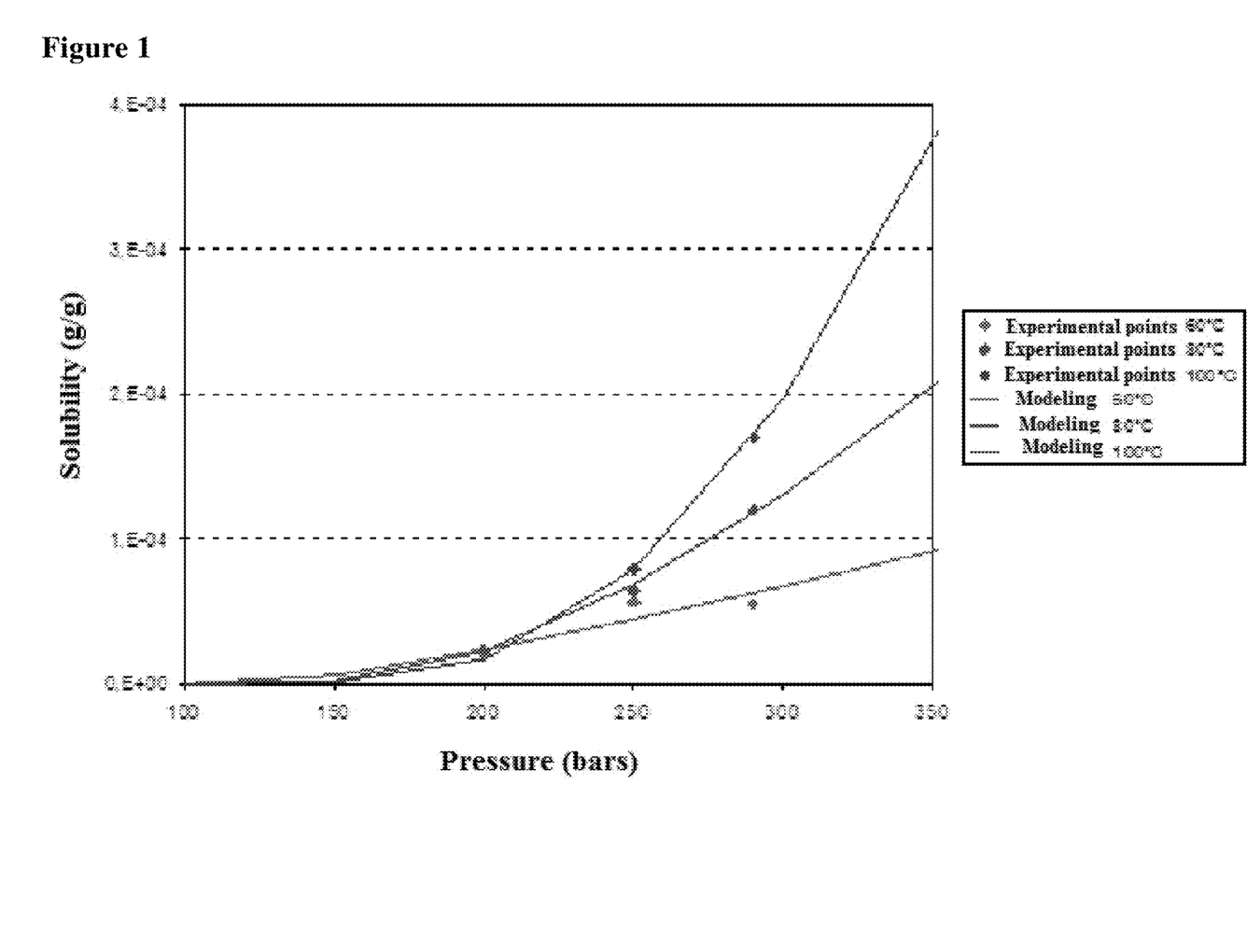
FIG. 1 is illustration of data relating to the solubility of modafinil in $CO_2$.

Thus, it has been realized that modafinil has acceptable solubility in $CO_2$ as shown in FIG. 1.

It was then sought to spray the dissolved active ingredient onto an inert support so as to have granules consisting of said support, at the surface of which particles of modafinil obtained according to the aforementioned method were absorbed. The grain size of these particles as well as the crystalline form of these same particles was subject to extensive study.

Several tests were conducted, first by using anhydrous lactose as a support.

Different samples were made by varying the parameters: extraction temperature and pressure, pre-expansion temperature, expansion pressure, percentage of liquid $CO_2$.

By studying the crystalline forms of the powders obtained by differential thermal analysis or X-ray diffraction and by comparing these same data with those of the literature, it may therefore be concluded that the profiles are identical and correspond to anhydrous lactose and to the IV form of racemic modafinil.

Dissolution was then studied in HPLC, baskets 50 rpm; dissolution medium: HCl 0.1 N; bath temperature: 37° C.;

volume: 450 ml; test sample equivalent to about 50 mg of S modafinil; Formulations put into gelatin capsules of size 000 (2 gelatin capsules).

Figure 2:
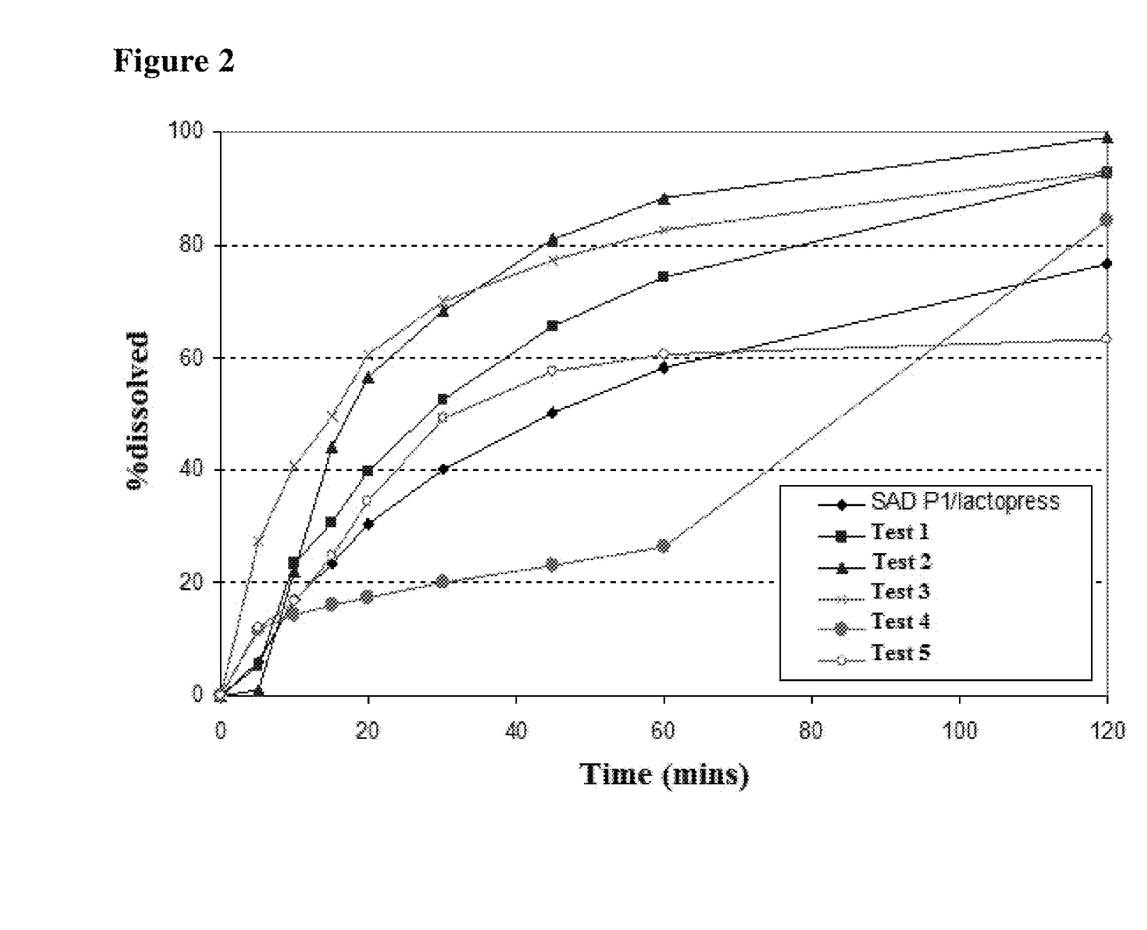
FIG. 2 is illustration of data relating to dissolution studied via HPLC.

The obtained results appear in FIG. 2:

An increase of the dissolution in vitro as compared with the mixture alone (SAD P1/lactopress) is observed.

Different parameters were then modified:
changing the support for mannitol,
increasing the loading level up to 30% of an active ingredient load
using S modafinil
a solvent other than $CO_2$, notably tetrafluoroethane, more specifically 1,1,1,2-tetrafluoroethane.

The table below repeats the result when using S modafinil, and mannitol instead of anhydrous lactose; further the loading level was increased to about 30%.

| Test | Amount of extracted modafinil (g) | Solubility (g/g) | Amount of collected formulation (g) | Collection yield (%) | Theoretical load levels (%) |
| --- | --- | --- | --- | --- | --- |
| Formulations prepared with supercritical $CO_2$ | | | | | |
| Formulation 1 | 10.0 | 1.0.E−04 | 29.54 | 96 | 32.65 |
| Formulation 2 | 9.5 | 9.3.E−05 | 29.40 | 98 | 31.52 |
| Formulation 3 | 9.7 | 9.9.E−05 | 29.62 | 98 | 32.18 |
| Formulations prepared with tetrafluoroethane | | | | | |
| Formulation 4 | 11.4 | 2.5.E−04 | 28.81 | 86 | 31.38 |
| Formulation 5 | 11.5 | 1.9.E−04 | 26.68 | 80 | 31.66 |
| Formulation 6 | 11.5 | 2.7.E−04 | 30.36 | 91 | 34.27 |

Figure 3:
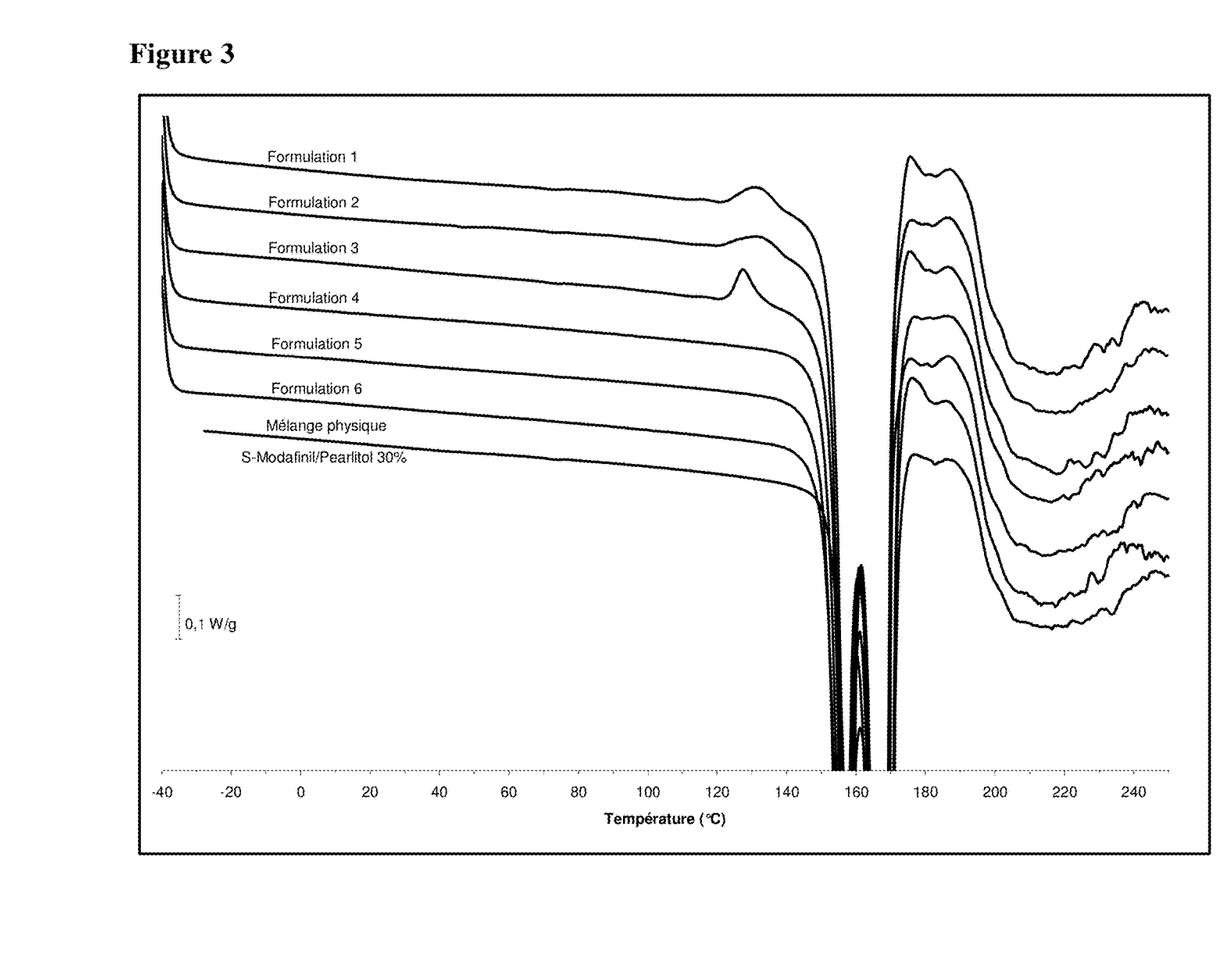
FIG. 3 is illustration of DSC profiles of formulations of the S-modafinil/mannitol type prepared with the supercritical $CO_2$ or tetrafluoroethane methods.
Figure 4:
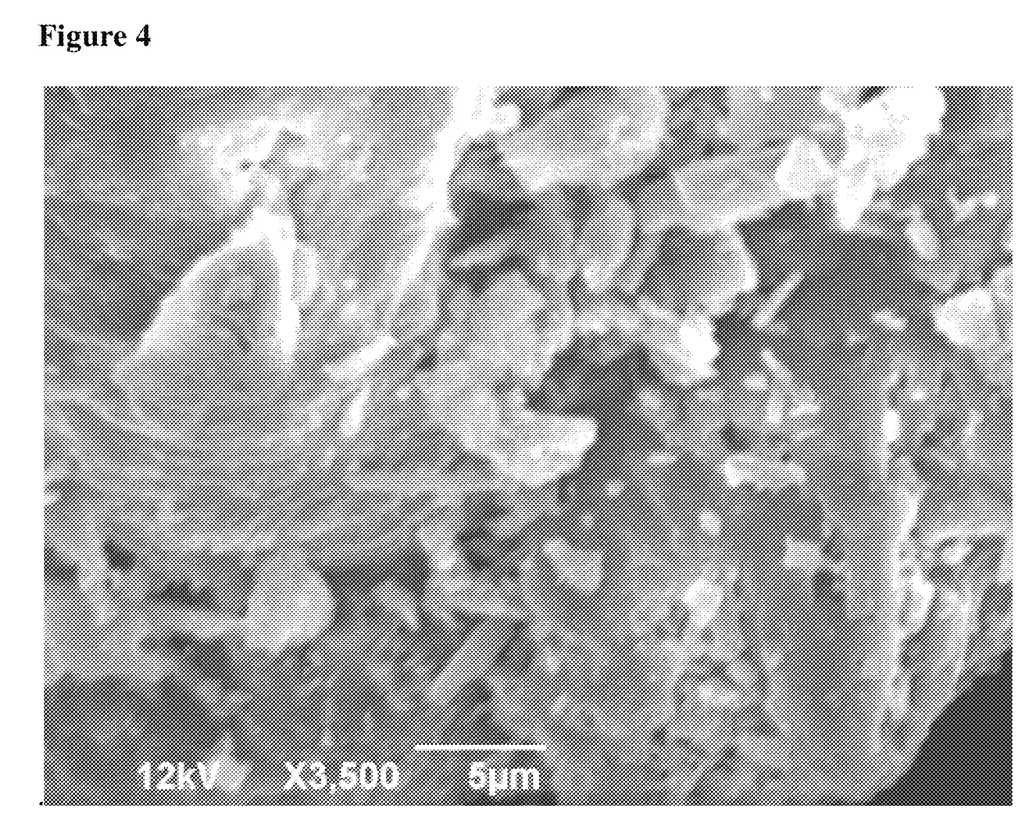
FIG. 4 is a micrograph of mannitol (Pearlitol 200SD) (X3500) obtained via scanning electron microscope (SEM)
Figure 5:
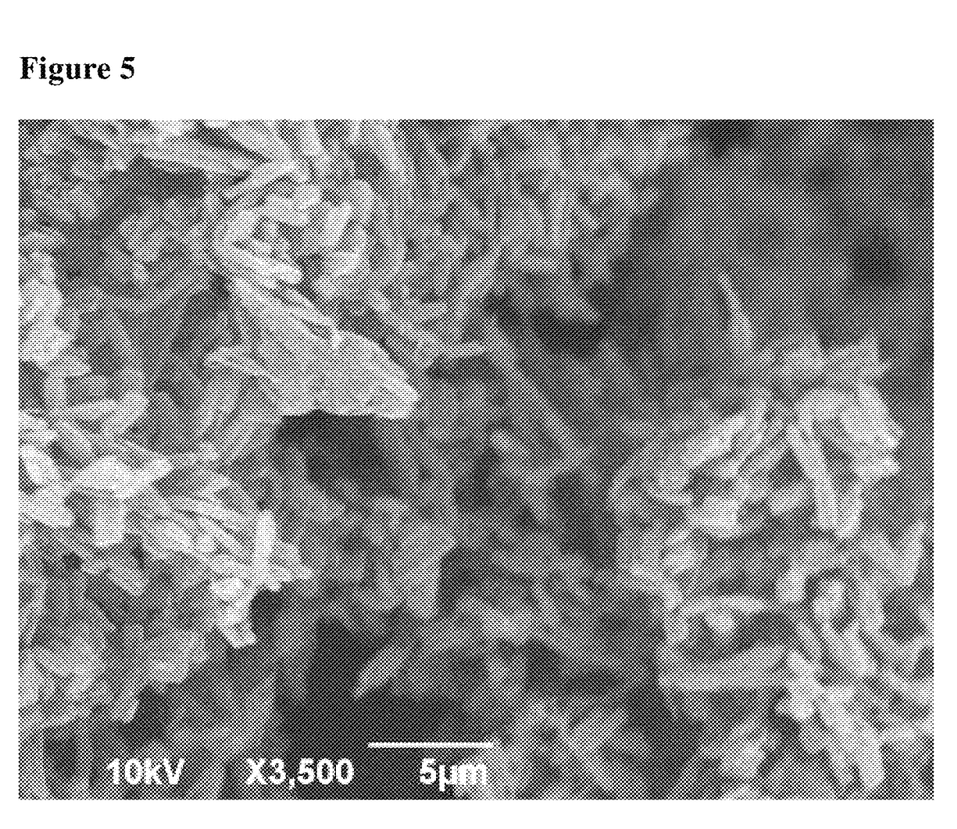
FIG. 5 is a micrograph of Sample 1 obtained via SEM X3500.
Figure 6:
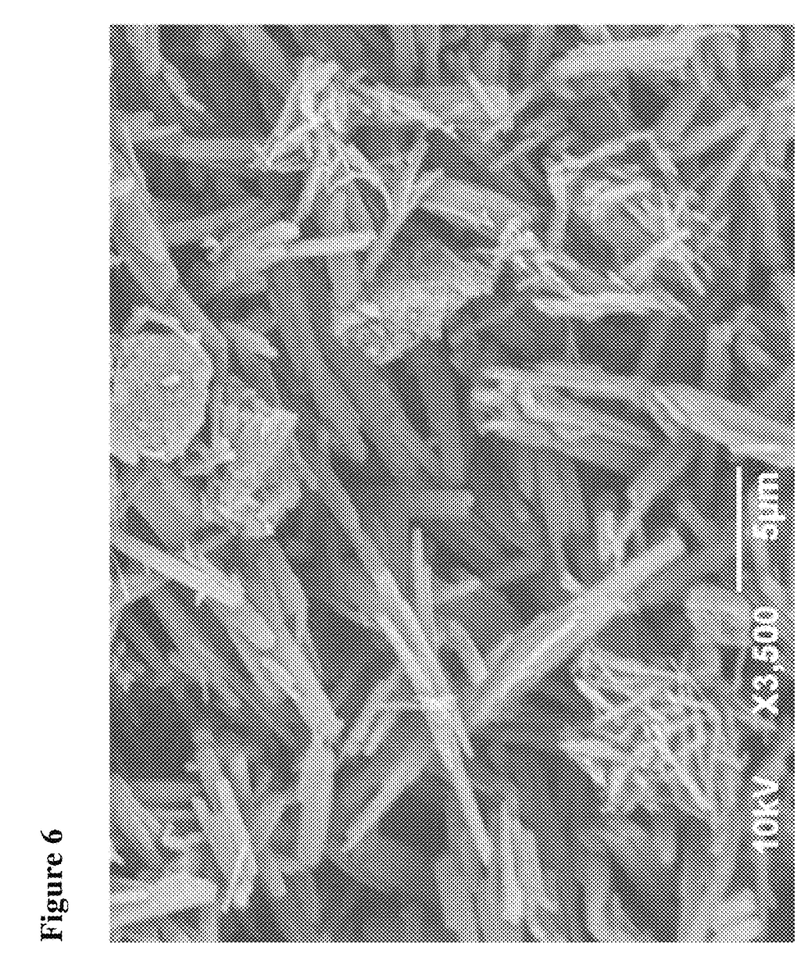
FIG. 6 is a micrograph of Sample 2 obtained via SEM X3500
Figure 7:
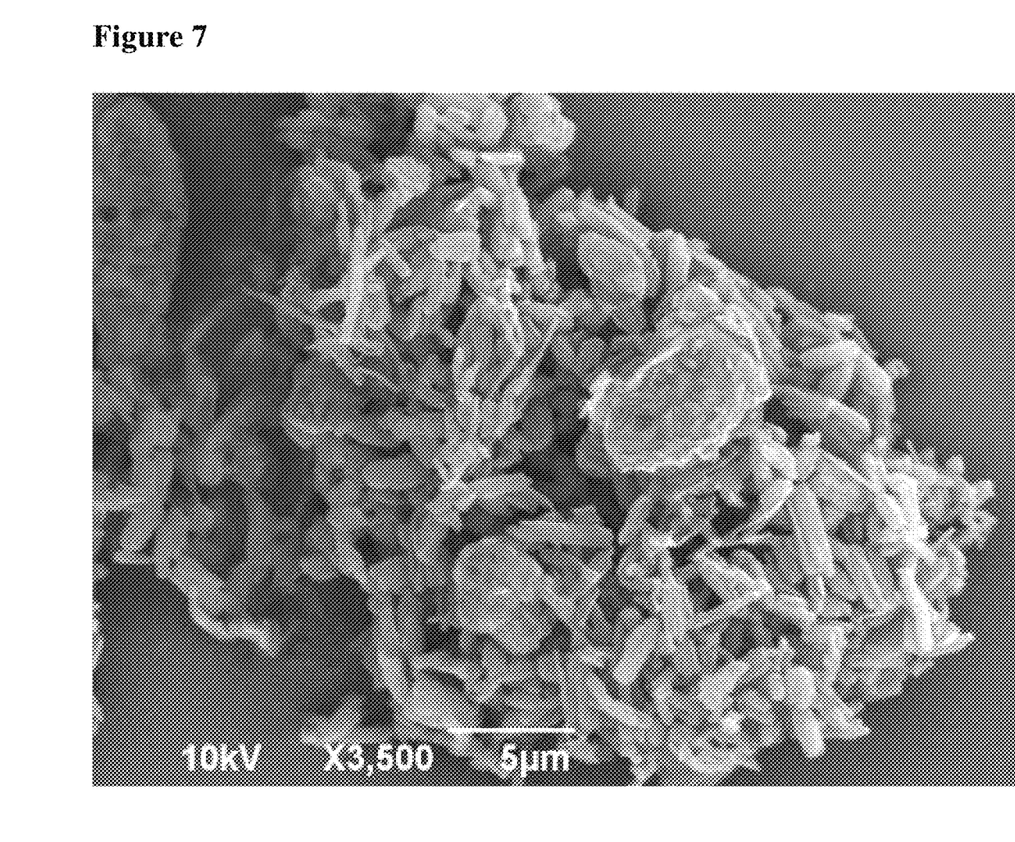
FIG. 7 is a micrograph of Sample 3 obtained via SEM X3500.
Figure 8:
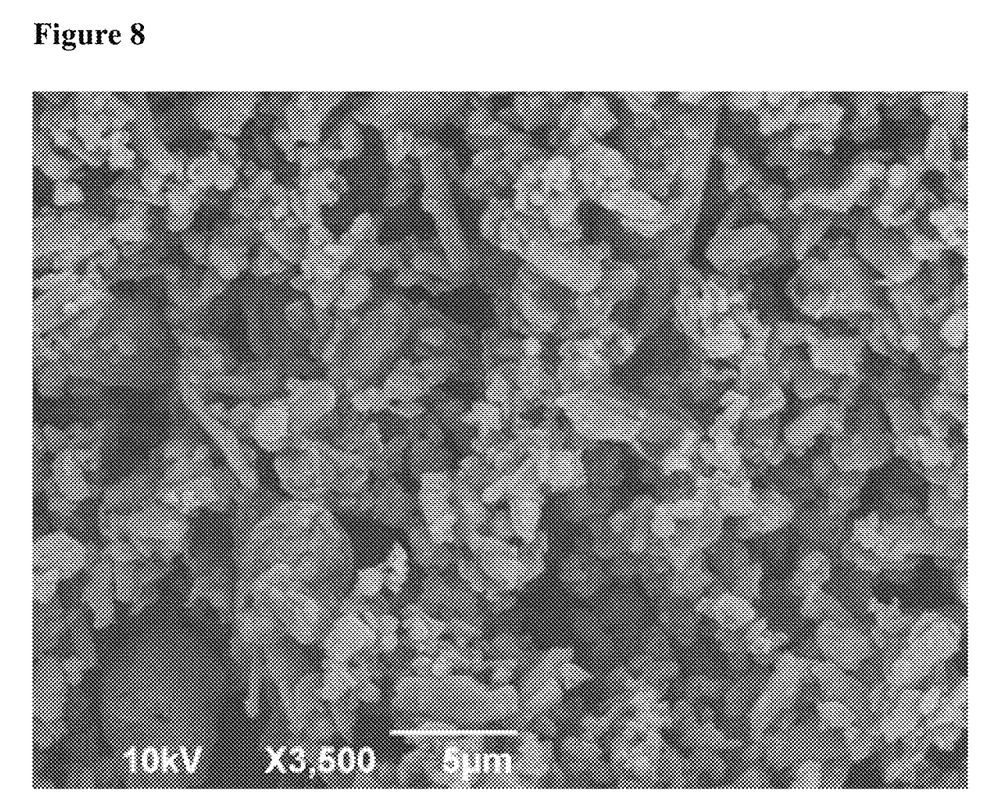
FIG. 8 is a micrograph of Sample 4 obtained via SEM X3500.
Figure 9:
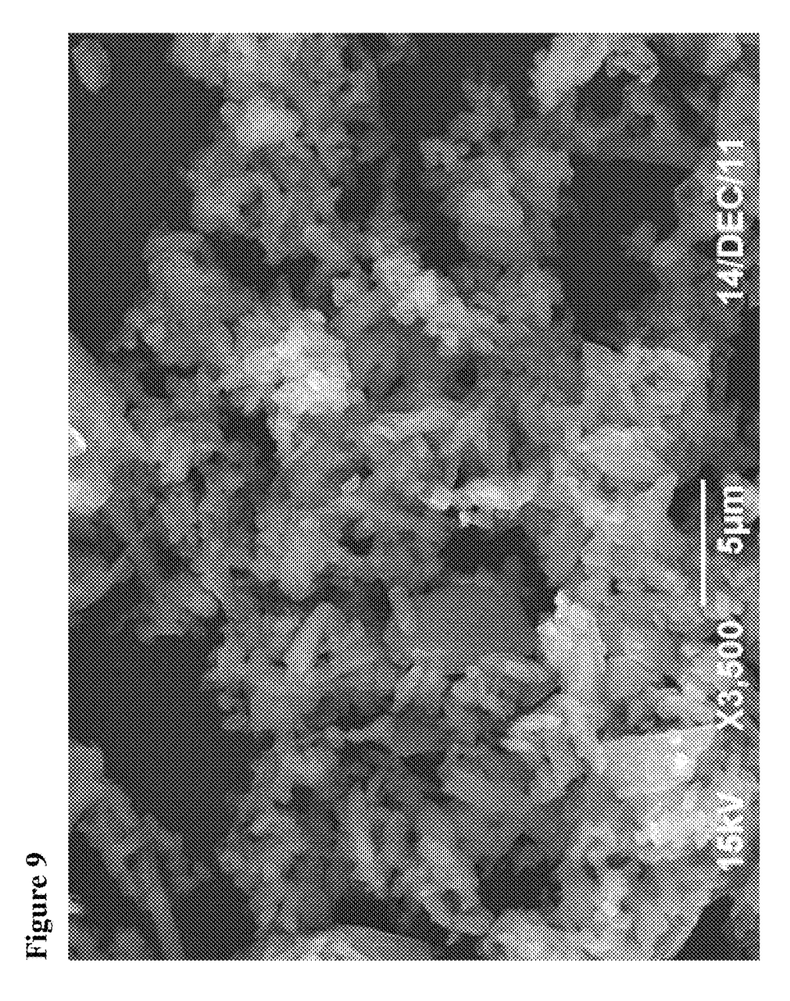
FIG. 9 is a micrograph of Sample 5 obtained via SEM X3500.

The curves in FIG. 3 illustrate the comparison of the DSC profiles of formulations of the S-modafinil/mannitol type prepared with the supercritical $CO_2$ or tetrafluoroethane methods with the reference physical mixture. The operating procedure for obtaining the modafinil entering these formulations is that of international application WO 2010/112702.

FIGS. 4-9 are different micrographs of S modafinil particles were obtained by means of a scanning electron microscope (SEM) from 30% S-modafinil/mannitol formulations; Sample 2 having been obtained with $CO_2$ as a supercritical solvent and Sample 4 with tetrafluoroethane.

Figure 10:
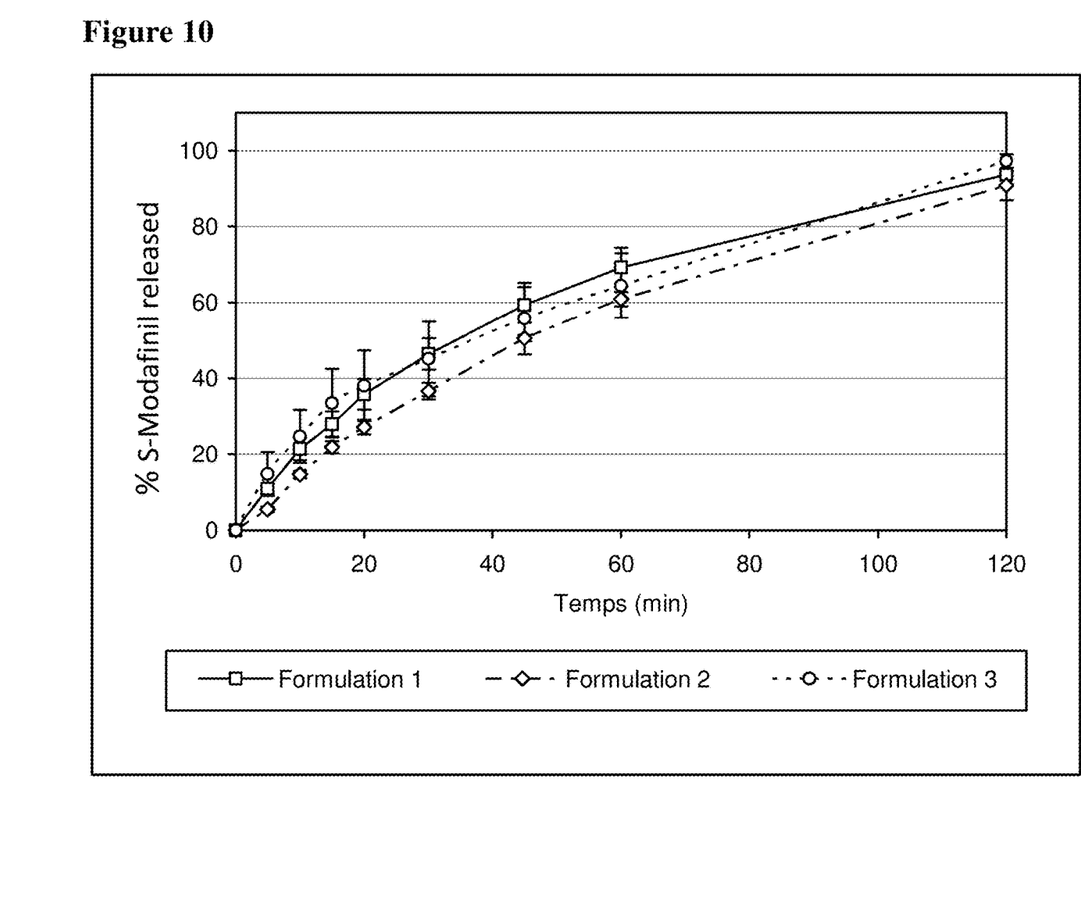
FIG. 10 is illustration of data relating to the comparison of the dissolution kinetics of the 30% S modafinil/mannitol formulations.
Figure 11:
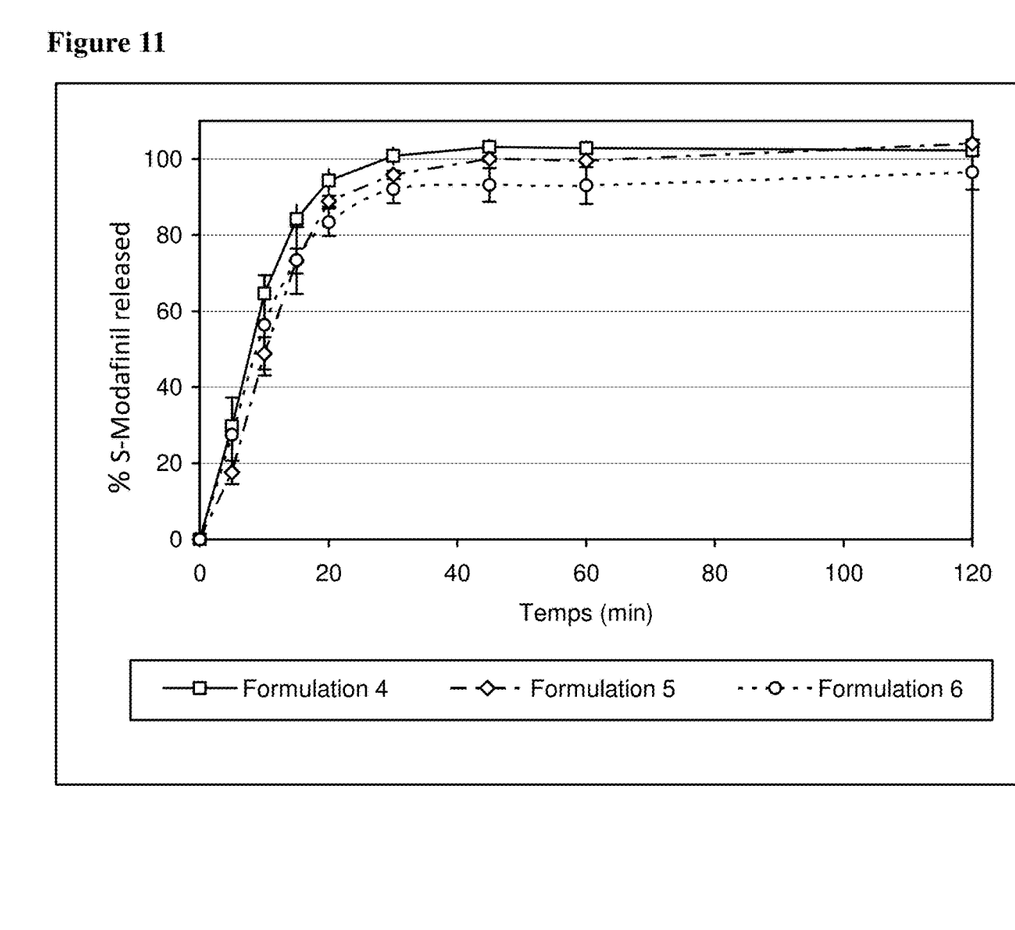
FIG. 11 is illustration of data relating to the comparison of the dissolution kinetics of the 30% S modafinil/mannitol formulations.

FIGS. 10 and 11 illustrate the comparison of the dissolution kinetics of the 30% S modafinil/mannitol formulations prepared with the supercritical $CO_2$ method (medium HCl 0.1N)—Sample 2—and by the method using tetrafluoroethane—Sample 4.

The analytical results of the formulations confirm the results obtained during the previous studies although the capture excipient has been changed:

preparation of uniform titer formulations with good capture efficiency for S-modafinil particles;

the DSC profiles are similar to the profiles of formulations prepared under the same operating conditions during the previous tasks;

SEM observations of the formulations seem to indicate that S modafinil is crystallized in the form of particles with a size of the order of one micrometer;

the dissolution kinetics are reproducible for both types of formulations and similar to the results obtained earlier. The dissolution rate of the supercritical $CO_2$ formulations is rather slow. Formulations with tetrafluoroethane have a faster dissolution profile.

The preparations obtained earlier were formulated so as to obtain tablets with a dose of 2 mg of S modafinil, these tablets being intended to be administered to the rat during a pharmacokinetic study.

The method used is the following:

after weighing each of the components, the excipients are successively introduced in an increasing weight order into a mixer;

the mixture is then sifted for removing the possible clusters;

the obtained mixture is then compacted and calibrated on a grid with an aperture of 1.25 mm at 250 rpm;

it is then proceeded with compression on a SVIAC compressing machine.

Formulation DASC00512:

| Raw materials | g | % |
| --- | --- | --- |
| Echantillon 4 | 5.000 | 55.64 |
| Aerosil 200 | 1.250 | 13.91 |
| PVP XL | 0.358 | 3.99 |
| PVP K30 | 0.765 | 8.51 |
| Pearlitol 400 DC | 1.523 | 16.95 |
| Magnesium stearate | 0.090 | 1.00 |
| TOTAL | 8.987 | 100.00 |

Figure 12:
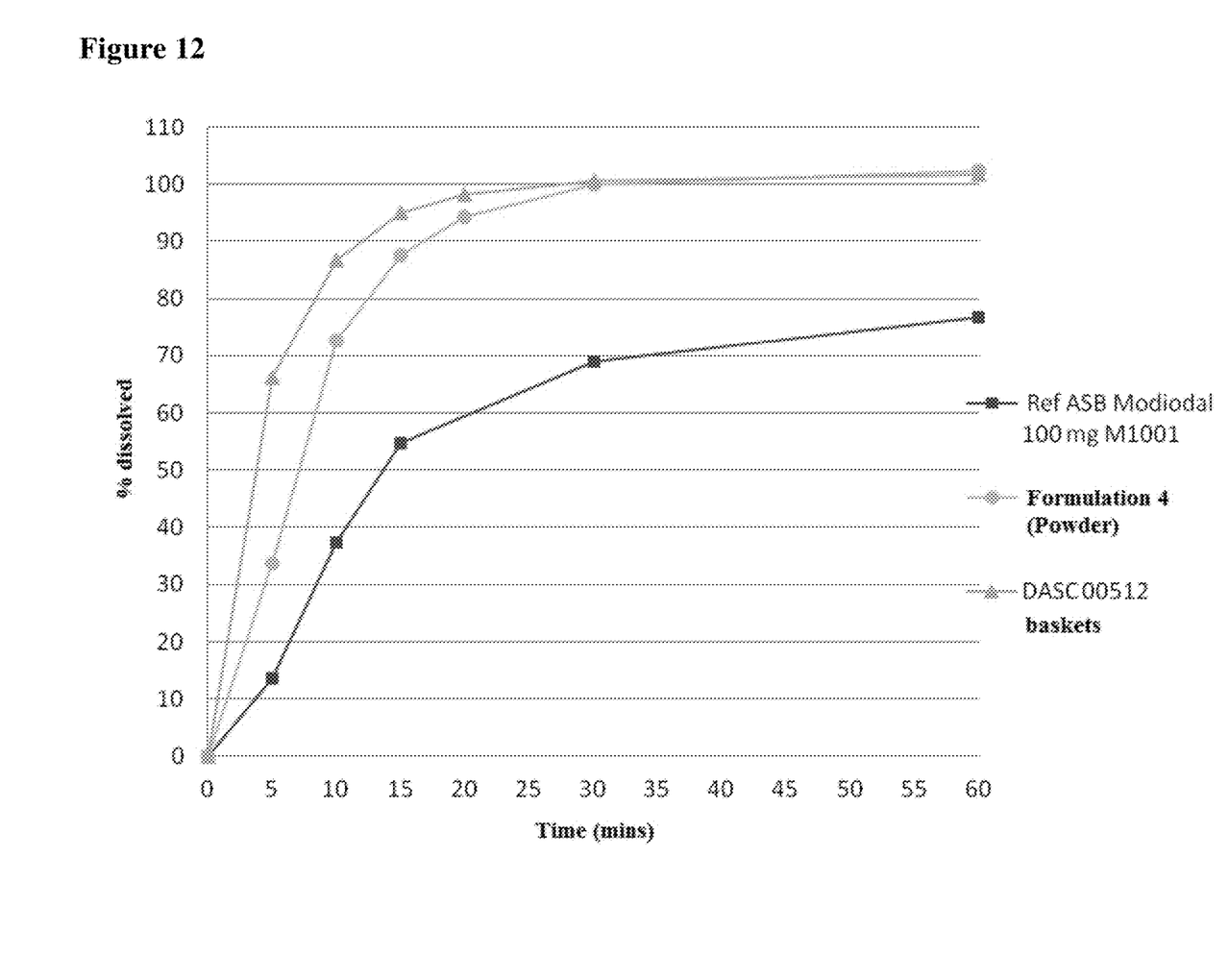
FIG. 12 is illustration of dissolution results where Modiodal, Formulation 4 (powder) and compound DASC 00512 (tablets dissolved in baskets) are compared.

The dissolution results are shown in FIG. 12 where Modiodal, Formulation 4 (powder) and compound DASC 00512 (tablets dissolved in baskets) are compared.

The S modafinil formulation obtained according to the supercritical fluid method actually confirms that it allows both very fast release (less than 1 hour) and an effect with limited duration (between 3 and 4 hours): it is this dual feature which makes the formulation according to the present invention, interesting.

This formulation consists in granules forming a support, for example mannitol or anhydrous lactose, or any other inert support on the surface of which S modafinil particles obtained with the supercritical fluid technology have been absorbed.

Advantageously, the obtained tablets from this formulation will be dosed between 25 and 200 mg of S modafinil, and even more advantageously between 50 and 100 mg. The aforementioned feature allows the use of these tablets as soon as the consumer needs increased alertness in the short term, i.e. very rapidly (less than one hour) for a short period (3 to 4 hours for example).

The invention claimed is:
1. A method for obtaining a S modafinil-based pharmaceutical composition, the method consisting of the following acts, which are performed successively:

solubilizing S modafinil in a fluid in the supercritical state in order to form a solution;

expanding the solution such that S modafinil is precipitated; and absorbing the precipitated S modafinil on an inert support in order to obtain granules.

2. The method according to claim 1, wherein the supercritical fluid is $CO_2$.

3. The method according to claim 1, wherein the supercritical fluid is tetrafluoroethane.

4. The method according to claim 1, wherein the inert support is mannitol.

5. The method according to claim 1, wherein the inert support is anhydrous lactose.

6. A pharmaceutical composition obtained according to the method according to claim 3, the pharmaceutical composition comprising S modafinil, wherein upon administration of the pharmaceutical composition to a patient the S modafinil of the pharmaceutical composition is released from the pharmaceutical composition in less than 1 hour, and a therapeutic effect of the pharmaceutical composition lasts for a duration of between 3 and 4 hours.

7. The pharmaceutical composition according to claim 6, wherein the pharmaceutical composition is in an oral form.

8. The pharmaceutical composition according to claim 7, wherein the oral form contains from 25 to 200 mg of the S modafinil.

9. The pharmaceutical composition according to claim 8, wherein the oral form contains from 50 to 100 mg of the S modafinil.

10. The pharmaceutical composition according to claim 7, wherein the oral form is a tablet.

* * * * *